United States Patent
Feiring et al.

(10) Patent No.: US 7,326,796 B2
(45) Date of Patent: Feb. 5, 2008

(54) FLUORINATED MONOMERS, FLUORINATED POLYMERS HAVING POLYCYCLIC GROUPS WITH FUSED 4-MEMBERED HETEROCYCLIC RINGS, USEFUL AS PHOTORESISTS, AND PROCESSES FOR MICROLITHOGRAPHY

(75) Inventors: Andrew E. Feiring, Wilmington, DE (US); Frank L. Schadt, III, Wilmington, DE (US); Viacheslav Alexandrovich Petrov, Hockessin, DE (US); Bruce Edmund Smart, Wilmington, DE (US); William Brown Farnham, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 471 days.

(21) Appl. No.: 10/523,489

(22) PCT Filed: Aug. 8, 2003

(86) PCT No.: PCT/US03/25021

§ 371 (c)(1),
(2), (4) Date: Feb. 3, 2005

(87) PCT Pub. No.: WO2004/014960

PCT Pub. Date: Feb. 19, 2004

(65) Prior Publication Data

US 2006/0167284 A1    Jul. 27, 2006

(51) Int. Cl.
*C07D 205/15* (2006.01)
*C07D 305/14* (2006.01)

(52) U.S. Cl. ............... 548/950; 548/952; 549/200; 549/510; 549/511

(58) Field of Classification Search ............... 548/950, 548/952; 549/200, 510, 511
See application file for complete search history.

(56) References Cited

U.S. PATENT DOCUMENTS 3,129,248 A    4/1964    England
3,538,059 A    11/1970   Beermann et al.
3,549,580 A    12/1970   Schmidt et al.
6,593,058 B1 *  7/2003   Feiring et al. ........... 430/270.1
6,849,377 B2 *  2/2005   Feiring et al. ........... 430/270.1

FOREIGN PATENT DOCUMENTS

WO    WO 00/17712 A1    3/2000
WO    WO 00/67072 A1    11/2000

OTHER PUBLICATIONS

E. Reichmanis et. al., "The Effect of Substituents on the Photosensitivity of 2-Nitrobenzyl Ester Deep UV Resists", J. Electrochem Soc., 1983, pp. 1433-1437, vol. 130.
C.D. Smith, Quadricyclane, Organic Synthesis, pp. 962-964, vol. 6.
V.A. Petrov et. al., Reaction OG Higher Perfluorinated Amines with Antimony Pentafluoride, An USSR, 1985, p. 1934.
W.J. Midleton et. al., Fluorimines, J. Org. Chem., 1965, pp. 1398-1402, vol. 30.
D.C. England et. al., J. Am. Chem. Soc., 1965, pp. 4019-4020, , vol. 87.
V.A. Petrov et. al., Unusual Reaction of N-Arylimines of Hexafluoroacetone with M-Chloroperoxybenzoic Acid. New Route to 2,2-Bis (Trifluoromethyl) Benzoxazolidines, Israel Journal of Chemistry, 1985, pp. 147-150, vol. 39.
PCT International Search Report Dated Dec. 22, 2004, International Appln. No. PCT/US03/25021, International Filing Date—Aug. 8, 2003, pp. (4).

* cited by examiner

*Primary Examiner*—Golam M. M. Shameem

(57) ABSTRACT

The present invention provides novel fluorine-containing copolymers which comprise at least one fluorinated olefin, at least one polycyclic ethylenically unsaturated monomer with a fused 4-membered heterocyclic ring and, optionally, other components. The copolymers are useful for photoimaging compositions and, in particular, photoresist compositions (positive-working and/or negative-working) for imaging in the production of semiconductor devices. The copolymers are especially useful in photoresist compositions having high UV transparency (particularly at short wavelengths, e.g., 157 nm) which are useful as base resins in resists and potentially in many other applications.

4 Claims, No Drawings

FLUORINATED MONOMERS, FLUORINATED POLYMERS HAVING POLYCYCLIC GROUPS WITH FUSED 4-MEMBERED HETEROCYCLIC RINGS, USEFUL AS PHOTORESISTS, AND PROCESSES FOR MICROLITHOGRAPHY

BACKGROUND OF THE INVENTION

The present invention relates to fluorine-containing copolymers which comprise at least one fluorinated olefin, at least one polycyclic ethylenically unsaturated monomer with a fused 4-membered heterocyclic ring and, optionally, other components. The copolymers are useful for photoimaging compositions and, in particular, photoresist compositions (positive-working and/or negative-working) for imaging in the production of semiconductor devices. The copolymers are especially useful in photoresist compositions having high UV transparency (particularly at short wavelengths, e.g., 157 nm) which are useful as base resins in resists and potentially in many other applications.

There is a critical need for resist compositions for use at 193 nm, and particularly at 157 nm, or lower that have not only high transparency at these short wavelengths but also suitable other key properties, including good plasma etch resistance and adhesive properties.

SUMMARY OF THE INVENTION

This invention provides an ethylenically unsaturated cyclic compound of structure:

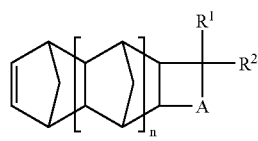

(I)

wherein n is 0, 1, or 2;
A is O or $NR^3$;
$R^1$ and $R^2$ are independently H; halogen; $C_1$-$C_{10}$ alkyl or alkoxy, optionally substituted by halogen or ether oxygen; $C_6$-$C_{20}$ aryl; Y; $C(R_f)(R_f')OR^4$; $R^5Y$; $OR^5Y$; and
$R^3$ is H; $C_1$-$C_{10}$ alkyl or alkoxy, optionally substituted by halogen or ether oxygens; $C_6$-$C_{20}$ aryl; Y; $C(R_f)(R_f')OR^4$; $R^5Y$; $OR^5Y$; or
$R^1$ and $R^2$ taken together are =$C(R_f)(R_f')$ or $C_2$-$C_9$ alkylene, optionally substituted by halogen or incorporating an ether oxygen; or
$R^2$ and $R^3$ taken together are part of a double bond;
Y is COZ or $SO_2Z$;
$R^4$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;
$R^5$ is a $C_1$-$C_{20}$ alkylene group, optionally substituted by halogen or ether oxygen;
Z is OH, halogen, $R^6$ or $OR^6$; and
$R^6$ is a $C_1$-$C_{20}$ alkyl group, optionally substituted by halogen or ether oxygens; or $C_6$-$C_{20}$ aryl;
with the proviso that at least one of $R^1$ or $R^2$ is fluorine or contains one or more fluorine atoms.

This invention also provides a polymer comprising:
(a) at least one repeat unit derived from an ethylenically unsaturated compound having at least one fluorine atom covalently attached to an ethylenically unsaturated carbon atom, and
(b) at least one repeat unit derived from an ethylenically unsaturated compound having the structure:

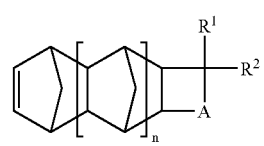

(I)

wherein n is 0, 1, or 2;
A is O or $NR^3$;
$R^1$ and $R^2$ are independently H; halogen; $C_1$-$C_{10}$ alkyl or alkoxy, optionally substituted by halogen or ether oxygen; $C_6$-$C_{20}$ aryl; Y; $C(R_f)(R_f')OR^4$; $R^5Y$; $OR^5Y$; and
$R^3$ is H; $C_1$-$C_{10}$ alkyl or alkoxy, optionally substituted by halogen or ether oxygens; $C_6$-$C_{20}$ aryl; Y; $C(R_f)(R_f')OR^4$; $R^5Y$; $OR^5Y$; or
$R^1$ and $R^2$ taken together are =$C(R_f)(R_f')$ or $C_2$-$C_9$ alkylene, optionally substituted by halogen or incorporating an ether oxygen; or
$R^2$ and $R^3$ taken together are part of a double bond;
Y is COZ or $SO_2Z$;
$R^4$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;
$R^5$ is a $C_1$-$C_{20}$ alkylene group, optionally substituted by halogen or ether oxygen;
Z is OH, halogen, $R^6$ or $OR^6$; and
$R^6$ is a $C_1$-$C_{20}$ alkyl group, optionally substituted by halogen or ether oxygens; or $C_6$-$C_{20}$ aryl.

This invention also provides a photoresist composition comprising:
(a) a fluorine-containing copolymer comprising:
(i) at least one repeat unit derived from an ethylenically unsaturated compound having at least one fluorine atom covalently attached to an ethylenically unsaturated carbon atom; and
(ii) at least one repeat unit derived from an ethylenically unsaturated cyclic compound having the structure:

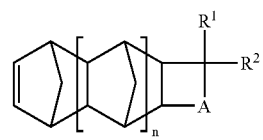

(I)

wherein n is 0, 1, or 2;
A is O or $NR^3$;
$R^1$ and $R^2$ are independently H; halogen; $C_1$-$C_{10}$ alkyl or alkoxy, optionally substituted by halogen or ether oxygen; $C_6$-$C_{20}$ aryl; Y; $C(R_f)(R_f')OR^4$; $R^5Y$; $OR^5Y$; and
$R^3$ is H; $C_1$-$C_{10}$ alkyl or alkoxy, optionally substituted by halogen or ether oxygens; $C_6$-$C_{20}$ aryl; Y; $C(R_f)(R_f')OR^4$;

$R^5Y$; $OR^5Y$; or $R^1$ and $R^2$ taken together are $=C(R_f)(R_f')$; or $R^1$ and $R^2$ taken together form a 3- to 9-membered carbocyclic or heterocyclic ring, optionally substituted by halogen, $C_1$-$C_5$ alkyl or $C_1$-$C_5$ fluoroalkyl groups; or $R^2$ and $R^3$ taken together are part of a double bond;

Y is COZ or $SO_2Z$;

$R^4$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

$R^5$ is a $C_1$-$C_{20}$ alkylene group, optionally substituted by halogen or ether oxygen;

Z is OH, halogen, $R^6$ or $OR^6$; and $R^6$ is a $C_1$-$C_{20}$ alkyl group, optionally substituted by halogen or ether oxygens; or $C_6$-$C_{20}$ aryl; and (b) a photoactive component.

This invention also provides a coated substrate comprising:

(a) a substrate; and (b) a photoresist composition comprising a fluorine-containing copolymer comprising:

(i) a fluorine-containing copolymer comprising:

(a') at least one repeat unit derived from an ethylenically unsaturated compound having at least one fluorine atom covalently attached to an ethylenically unsaturated carbon atom; and (b') at least one repeat unit derived from an ethylenically unsaturated cyclic compound having the structure:

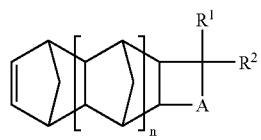

(I)

wherein n is 0, 1, or 2;

A is O or $NR^3$;

$R^1$ and $R^2$ are independently H; halogen; $C_1$-$C_{10}$ alkyl or alkoxy, optionally substituted by halogen or ether oxygen;

$C_6$-$C_{20}$ aryl; Y; $C(R_f)(R_f')OR^4$; $R^5Y$; $OR^5Y$; and $R^3$ is H; $C_1$-$C_{10}$ alkyl or alkoxy, optionally substituted by halogen or ether oxygens; $C_6$-$C_{20}$ aryl; Y; $C(R_f)(R_f')OR^4$;

$R^5Y$; $OR^5Y$; or $R^1$ and $R^2$ taken together are $=C(R_f)(R_f')$ or $C_2$-$C_9$ alkylene, optionally substituted by halogen or incorporating an ether oxygen; or $R^2$ and $R^3$ taken together are part of a double bond;

Y is COZ or $SO_2Z$;

$R^4$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

$R^5$ is a $C_1$-$C_{20}$ alkylene group, optionally substituted by halogen or ether oxygen;

Z is OH, halogen, $R^6$ or $OR^6$; and $R^6$ is a $C_1$-$C_{20}$ alkyl group, optionally substituted by halogen or ether oxygens; or $C_6$-$C_{20}$ aryl; and (ii) a photoactive component.

DETAILED DESCRIPTION

Fluorinated Monomers

A fluorinated monomer of this invention is an ethylenically unsaturated cyclic compound of structure:

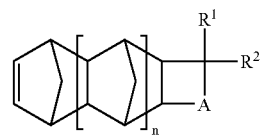

(I)

wherein n is 0, 1, or 2;

A is O or $NR^3$;

$R^1$ and $R^2$ are independently H; halogen; $C_1$-$C_{10}$ alkyl or alkoxy, optionally substituted by halogen or ether oxygen; $C_6$-$C_{20}$ aryl; Y; $C(R_f)(R_f')OR^4$; $R^5Y$; $OR^5Y$; and $R^3$ is H; $C_1$-$C_{10}$ alkyl or alkoxy, optionally substituted by halogen or ether oxygens; $C_6$-$C_{20}$ aryl; Y; $C(R_f)(R_f')OR^4$; $R^5Y$; $OR^5Y$; or $R^1$ and $R^2$ taken together are $=C(R_f)(R_f')$ or $C_2$-$C_9$ alkylene, optionally substituted by halogen or incorporating an ether oxygen; or $R^2$ and $R^3$ taken together are part of a double bond;

Y is COZ or $SO_2Z$;

$R^4$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

$R^5$ is a $C_1$-$C_{20}$ alkylene group, optionally substituted by halogen or ether oxygen;

Z is OH, halogen, $R^6$ or $OR^6$; and $R^6$ is a $C_1$-$C_{20}$ alkyl group, optionally substituted by halogen or ether oxygens; or $C_6$-$C_{20}$ aryl;

with the proviso that at least one of $R^1$ or $R^2$ is fluorine or contains one or more fluorine atoms.

One use of these monomers is in the preparation of the copolymers described below.

Fluorinated Copolymers

A fluorine-containing copolymer of this invention comprises at least one repeat unit (discussed infra) derived from at least one ethylenically unsaturated compound containing at least one fluorine atom attached to an ethylenically unsaturated carbon atom; and at least one repeat unit derived from an ethylenically unsaturated compound of structure (I):

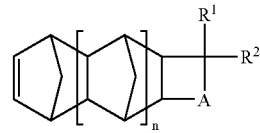

(I)

wherein n is 0, 1, or 2;

A is O or $NR^3$;

$R^1$ and $R^2$ are independently H; halogen; $C_1$-$C_{10}$ alkyl or alkoxy, optionally substituted by halogen or ether oxygen; $C_6$-$C_{20}$ aryl; Y;

$C(R_f)(R_f')OR^4$; $R^5Y$; $OR^5Y$; and $R^3$ is H; $C_1$-$C_{10}$ alkyl or alkoxy, optionally substituted by halogen or ether oxygens; $C_6$-$C_{20}$ aryl; Y; $C(R_f)(R_f')OR^4$; $R^5Y$; $OR^5Y$; or $R^1$ and $R^2$ taken together are $=C(R_f)(R_f')$ or $C_2$-$C_9$ alkylene, optionally substituted by halogen or incorporating an ether oxygen; or $R^2$ and $R^3$ taken together are part of a double bond;

Y is COZ or $SO_2Z$;

$R^4$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

$R^5$ is a $C_1$-$C_{20}$ alkylene group, optionally substituted by halogen or ether oxygen;

Z is OH, halogen, $R^6$ or $OR^6$; and $R^6$ is a $C_1$-$C_{20}$ alkyl group, optionally substituted by halogen or ether oxygens; or $C_6$-$C_{20}$ aryl.

Preferred compounds of structure (I) are those in which n is zero, A is oxygen, and $R^1$ and $R^2$ are selected from the group consisting of perfluoroalkyl and $CO_2R^6$, wherein $R^6$ is a $C_1$-$C_{20}$ alkyl group.

Some illustrative, but nonlimiting, examples of representative monomers of structure (I) and within the scope of the invention are presented below:

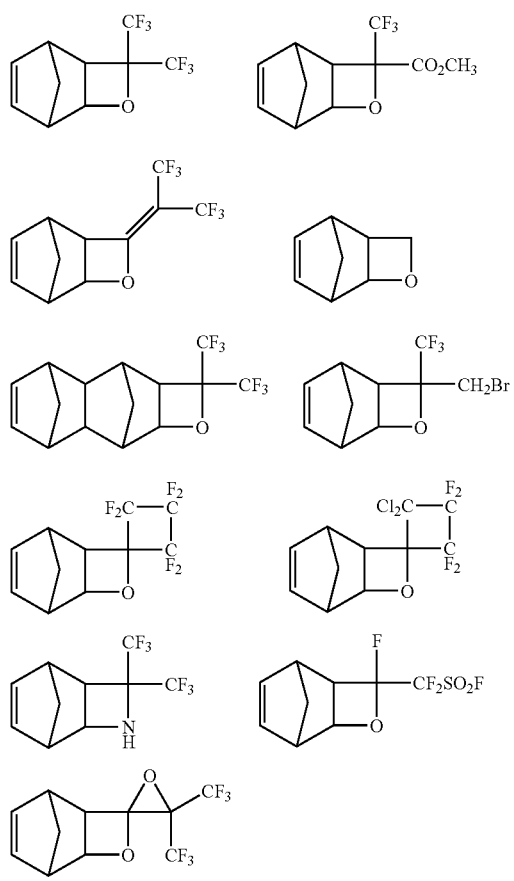

Compounds of structure (I) wherein n 0 may be prepared by thermal cycloaddition reaction of unsaturated compounds of structure (II) with quadricyclane (tetracyclo[2.2.1.0$^{2,6}$ 0$^{3,5}$]heptane) as shown in the equation below and illustrated by the examples.

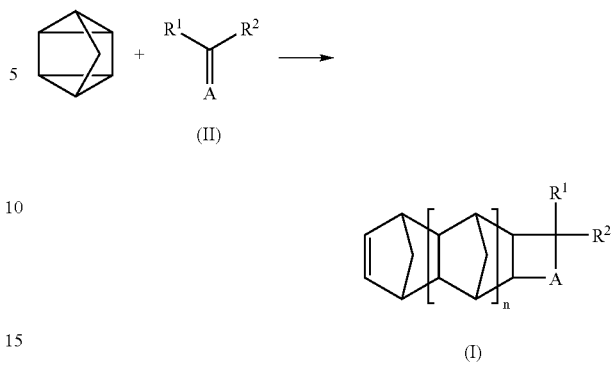

The reaction may be conducted at temperatures ranging from about −50° C. to about 200° C., more typically from about 0° C. to about 150° C. in the absence or presence of an inert solvent such as diethyl ether. For reactions conducted at or above the boiling point of one or more of the reagents or solvent, a closed reactor is typically used to avoid loss of volatile components. Compounds of structure (I) in which n=1 or 2 can be prepared by reaction of compounds of structure (I) with n=0 with cyclopentadiene, as is known in the art.

Compounds of structure (I) can be prepared by reaction of compounds structure (II) with bicyclo[2.2.1]hepta-2,5-diene under UV irradiation, optionally in the presence of a photosensitizer that is compatible with II, for example acetophenone.

The fluorine-containing copolymer also comprises a repeat unit derived from at least one ethylenically unsaturated compound (a fluoro-olefin) containing at least one fluorine atom attached to an ethylenically unsaturated carbon. The fluoro-olefin comprises 2 to 20 carbon atoms. Representative fluoro-olefins include, but are not limited to, tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene-4-methyl-1,3-dioxolane), $CF_2=CFO(CF_2)_tCF=CF_2$, where t is 1 or 2, and $R_f''OCF=CF_2$ wherein $R_f''$ is a saturated fluoroalkyl group of from 1 to 10 carbon atoms. A preferred fluoro-olefin is tetrafluoroethylene.

The copolymers of this invention can further comprise one or more additional repeat units derived from other comonomers. For example, the copolymer of this invention can also comprise a fluoroalcohol group. The fluoroalcohol group can be derived from at least one ethylenically unsaturated compound containing a fluoroalcohol group having the structure:

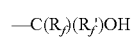

wherein $R_f$ and $R_f'$ are the same or different fluoroalkyl groups of from 1 to 10 carbon atoms, or taken together are $(CF_2)_m$ wherein m is 2 to 10. $R_f$ and $R_f'$ can be partially fluorinated alkyl groups or fully fluorinated alkyl groups (i.e., perfluoroalkyl groups). The term "taken together" indicates that $R_f$ and $R_f'$ are not separate, discrete fluorinated alkyl groups, but that together they form a ring structure such as is illustrated below in case of a 5-membered ring:

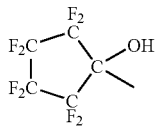

$R_f$ and $R_f'$ can be partially fluorinated alkyl groups without limit according to the invention except that there must be a sufficient degree of fluorination present to impart acidity to the hydroxyl (—OH) of the fluoroalcohol functional group, such that the hydroxyl proton is substantially removed in basic media, such as in aqueous sodium hydroxide solution or tetraalkylammonium hydroxide solution. In preferred cases according to the invention, there will be sufficient fluorine substitution present in the fluorinated alkyl groups of the fluoroalcohol functional group such that the hydroxyl group will have a pKa of 5 to 11. Preferably, $R_f$ and $R_f'$ are independently perfluoroalkyl groups of 1 to 5 carbon atoms; $R_f$ and $R_f'$ most preferably, $R_f$ and $R_f'$ are both trifluoromethyl ($CF_3$).

The fluorinated copolymers, photoresists, and processes of this invention that contain a fluoroalcohol functional group can have the structure:

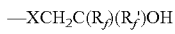

wherein $R_f$ and $R_f'$ are as described above, X is an element from Group VA and VIA of the Periodic Table of the Elements (CAS Version), for example, oxygen, sulfur, nitrogen and phosphorous. Oxygen is the preferred X group.

Some illustrative, but nonlimiting, examples of representative comonomers containing a fluoroalcohol functional group and within the scope of the invention are presented below:

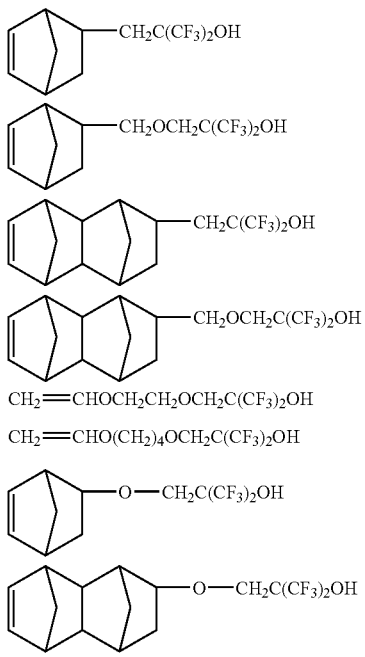

The copolymer can further comprise at least one acid-containing or protected acid-containing structural unit:

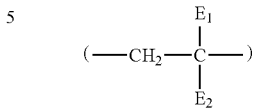

wherein $E_1$ is H or $C_1$-$C_{12}$ alkyl; $E_2$ is $CO_2E_3$, $SO_3E$, or other acidic group; and E and $E_3$ are H, or unsubstituted or heteroatom substituted $C_1$-$C_{12}$ alkyl. Suitable heteroatoms include oxygen, nitrogen, sulfur, halogen and phosphorus. When the heteroatom is oxygen, the substituent can contain a hydroxyl group. Alkyl groups can contain one to twelve carbon atoms, preferably one to eight. A preferred acid-containing polymer for aqueous processability (aqueous development) in use, particularly as a binder in a photoresist composition, is a carboxylic acid-containing copolymer. The level of carboxylic acid groups is typically determined for a given photoresist composition by optimizing the amount needed for good development in aqueous alkaline developer. The additional monomers can be acrylates. Tertiary alkyl acrylates such as tert-butyl acrylate, 2-methyl-2-adamantyl acrylate and 2-methyl-2-norbornyl acrylate may provide acid sensitive functionality for image formation as discussed above. Other acrylates, such as acrylic acid, methyl acrylate, ethyl acrylate, propyl acrylate, 2-hydroxyethyl acrylate, 2-methoxyethyl acrylate, 2-cyanoethyl acrylate, glycidyl acrylate and 2,2,2-trifluoroethyl acrylate can be employed to modify the adhesion or solubility of the polymer especially when used in a photoresist composition. In one embodiment, tert-butylacrylate can be incorporated into the polymer to provide acid-labile tert-butyl ester groups.

Polar monomers such as vinyl acetate can also be incorporated into the copolymer in order to assist aqueous development or otherwise modify polymer properties.

The fluoroalcohol group and/or other acid group of the polymer can contain a protecting group that protects the fluorinated alcohol group and/or other acid group (i.e., the protected group) from exhibiting its acidity while in this protected form. As one illustrative example, the tertiary-butyl group is the protecting group in a tertiary-butyl ester and this protecting group protects the free acid. In undergoing deprotection (conversion of protected acid to free acid), the ester is converted to the corresponding acid.

An alpha-alkoxyalkyl ether group is a preferred protecting group for the fluoroalcohol group in order to maintain a high degree of transparency in the photoresist composition. The resulting protected fluoroalcohol group has the structure:

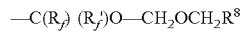

In this protected fluoroalcohol, $R_f$ and $R_f'$ are as described above; $R^8$ is hydrogen or a linear or branched alkyl group of between 1 and 10 carbon atoms. An illustrative, but non-limiting example, of an alpha-alkoxyalkyl ether group, which is effective as a protecting group in a protected acid group, is methoxy methyl ether (MOM). A protected fluoroalcohol with this particular protecting group can be obtained by reaction of chloromethylmethyl ether with the fluoroalcohol.

The fluoroalcohol functional group (protected or unprotected) of this invention can be used alone or in combination with one or more other acid groups, such as a carboxylic acid functional group (unprotected) or a t-butyl ester of carboxylic acid functional group (protected).

In this invention, often, but not always, the components having protected groups are repeat units having protected acid groups that have been incorporated into the polymer. Frequently the protected acid groups are present in one or more comonomers that are polymerized to form the copolymer of this invention. Alternatively, in this invention, a copolymer can be formed by copolymerization with an acid-containing comonomer and then subsequently acid functionality in the resulting acid-containing copolymer can be partially or wholly converted by appropriate means to derivatives having protected acid groups.

The preferred process for polymerizing the fluorine-containing copolymers of this invention is radical addition polymerization. Any suitable polymerization initiator, such as di-(4-tert-butylcyclohexyl)peroxy-dicarbonate, can be used under appropriate conditions. The polymerization pressure can range from about 50 to about 10,000 psig, preferably from about 200 to about 1,000 psig. The polymerization temperature can range from about 30° C. to about 120° C., preferably from about 40° C. to about 80° C. Suitable solvents include 1,1,2-trichlorofluoroethane and non-chlorofluorocarbon solvents such as 1,1,1,3,3-pentafluorobutane. The polymerization process is further enhanced by a semibatch synthesis. In the semibatch synthesis, a part of the monomer mixture is placed in the reaction vessel and then, portionwise or continuously, the remaining monomers and initiator are added to the vessel throughout the polymerization process.

Photoresist Development

Protective Groups for Removal by PAC Catalysis

Photoactive Component (PAC)

The photoresist compositions of this invention contain at least one photoactive component (PAC) that can produce either acid or base upon exposure to actinic radiation during the development process. If an acid is produced upon exposure to actinic radiation, the PAC is termed a photoacid generator (PAG). If a base is produced upon exposure to actinic radiation, the PAC is termed a photobase generator (PBG).

Suitable photoacid generators for this invention include, but are not limited to, 1) sulfonium salts (structure III), 2) iodonium salts (structure IV), and 3) hydroxamic acid esters, such as structure V.

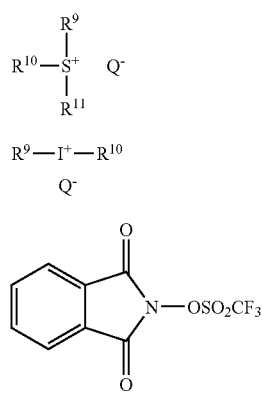

III

IV

V

In structures III to IV, $R^9$ to $R^{11}$ are, independently, substituted or unsubstituted $C_6$ to $C_{20}$ aryl, or substituted or unsubstituted $C_7$-$C_{40}$ alkylaryl or aralkyl. Representative aryl groups include, but are not limited to, phenyl, naphthyl, and anthracenyl. Suitable heteroatom substituents include, but are not limited to one or more oxygen, nitrogen, halogen or sulfur atoms. When the heteroatom is oxygen, the substituent can contain hydroxyl (—OH) or $C_1$-$C_{20}$ alkyloxy (e.g., $C_{10}H_{21}O$). The anion $Q^-$ in structures III-IV can be, but is not limited to, $SbF_6$— (hexafluoroantimonate), $CF_3SO_3$— (trifluoromethylsulfonate=triflate), and $C_4F_9SO_3$— (perfluorobutylsulfonate).

Functionality for Development

For use in a photoresist composition, the fluorine-containing copolymer should contain sufficient functionality to render the photoresist developable so as to produce a relief image, following imagewise exposure to ultraviolet radiation having wavelength of ≦365 nm. In some preferred embodiments, the sufficient functionality is selected from an acid and/or a protected acid group, as described above. Such acid or protected acid groups have been found to render the exposed portions of photoresist soluble in basic solution upon exposure to sufficient ultraviolet radiation having a wavelength of ≦365 nm while the unexposed portions are insoluble in the basic solution.

For development, one or more groups within the fluorine-containing copolymers should contain one or more components having protected acid groups that can yield, by catalysis of acids or bases generated photolytically from the photoactive compound (PAC), hydrophilic acid or base groups.

A given protected acid group is one that is normally chosen on the basis of its being acid labile, such that when photoacid is produced upon imagewise exposure, the acid will catalyze deprotection and production of hydrophilic acid groups that are necessary for development under aqueous conditions. In addition, the fluorine-containing copolymers may also contain acid functionality that is not protected.

Examples of basic developer include but are not limited to sodium hydroxide solution, potassium hydroxide solution, or ammonium hydroxide solution. Specifically a basic developer is an aqueous alkaline liquid such as a wholly aqueous solution containing 0.262 N tetramethylammonium hydroxide (with development at 25° C. usually for ≦2 min) or 1% sodium carbonate by weight (with development at a temperature of 30° C. usually for ≦2 min).

When an aqueous processable photoresist is coated or otherwise applied to a substrate and imagewise exposed to UV light, development of the photoresist composition may require that the binder material contain sufficient acid groups (e.g., carboxylic acid groups) and/or protected acid groups that are at least partially deprotected upon exposure to render the photoresist (or other photoimageable coating composition) processable in aqueous alkaline developer.

In one embodiment of this invention, the copolymer having one or more protected acid groups yield a carboxylic acid as the hydrophilic group upon exposure to photogenerated acid. Such protected acid groups include, but are not limited to, A) esters capable of forming, or rearranging to, a tertiary cation, B) esters of lactone, C) acetal esters, D) β-cyclic ketone esters, E) α-cyclic ether esters, and F) MEEMA (methoxy ethoxy ethyl methacrylate) and other esters which are easily hydrolyzable because of anchimeric assistance. Some specific examples in category A) are t-butyl ester, 2-methyl-2-adamantyl ester, and isobornyl ester.

A typical acidic group is the hekafluoroisopropanol group which may be incorporated by use of hexafluoroisopropanol-containing monomers as illustrated by examples.

Some or all of the hexafluoroisopropanol groups may be protected as, for example, acid-labile alkoxymethyl ethers or tert-butylcarbonates.

Examples of components having protected acid groups that yield an alcohol as the hydrophilic group upon exposure to photogenerated acid or base include, but are not limited to, t-butoxycarbonyl (t-BOC), t-butyl ether, and 3-cyclohexenyl ether.

In the case of a negative-working photoresist layer, the photoresist layer will be removed during development in portions which are unexposed to UV radiation but will be substantially unaffected in exposed portions during development using either a critical fluid or an organic solvent.

Dissolution Inhibitors and Additives

Various dissolution inhibitors can be utilized in this invention. Ideally, dissolution inhibitors (DIs) for far and extreme UV resists (e.g., 193 nm resists) should be designed/chosen to satisfy multiple materials needs including dissolution inhibition, plasma etch resistance, and adhesion behavior of resist compositions comprising a given DI additive. Some dissolution inhibiting compounds also serve as plasticizers in resist compositions.

A variety of bile-salt esters (i.e., cholate esters) are particularly useful as DIs in the compositions of this invention. Bile-salt esters are known to be effective dissolution inhibitors for deep UV resists, beginning with work by Reichmanis et al. in 1983. (E. Reichmanis et al., "The Effect of Substituents on the Photosensitivity of 2-Nitrobenzyl Ester Deep UV Resists", *J. Electrochem. Soc.* 1983, 130, 1433-1437.) Bile-salt esters are particularly attractive choices as DIs for several reasons, including their availability from natural sources, their high alicyclic carbon content, and particularly for their transparency in the deep and vacuum UV region, (which essentially is also the far and extreme UV region), of the electromagnetic spectrum. Typically, they are highly transparent at 193 nm. Furthermore, the bile-salt esters are also attractive DI choices since they may be designed to have widely ranging hydrophobic to hydrophilic compatibilities depending upon hydroxyl substitution and functionalization.

Representative bile-acids and bile-acid derivatives that are suitable as additives and/or dissolution inhibitors for this invention include, but are not limited to cholic acid, deoxycholic acid, lithocholic acid, t-butyl deoxycholate, t-butyl lithocholate, and t-butyl-3-α-acetyl lithocholate.

The invention is not limited to use of bile-acid esters and related compounds as dissolution inhibitors. Other types of dissolution inhibitors, such as various diazonaphthoquinones (DNQs) and diazocoumarins(DCs), can be utilized in this invention in some applications. Diazanaphthoquinones and diazocoumarins are generally suitable in resists compositions designed for imaging at higher wavelengths of UV light (e.g., 365 nm and perhaps at 248 nm). These dissolution inhibitors are generally not preferred in resist compositions designed for imaging with UV light at 193 nm or lower wavelengths, since these compounds absorb strongly in this region of the UV and are usually not sufficiently transparent for most applications at these low UV wavelengths.

Solvents

Photoresists of this invention are prepared as coating compositions by dissolving the components of the photoresist in a suitable solvent, for example, ether esters such as propyleneglycol monomethyl ether acetate, 2-ethoxyethyl acetate, 2-methoxyethyl acetate, and ethyl 3-ethoxypropionate; ketones such as cyclohexanone, 2-heptanone, and methyl ethyl ketone; esters such as butyl acetate, ethyl lactate, methyl lactate, and ethyl acetate; glycol ethers such as propylene glycol monomethyl ether, ethylene glycol monomethyl ether, ethyleneglycol monoethyl ether, and 2-methoxyethyl ether (diglyme); unsubstituted and substituted hydrocarbons and aromatic hydrocarbons such as hexane, toluene, and chlorobenzene; and fluorinated solvents such as CFC-113 (1,1,2-trichlorotrifluoromethane, E. I. du Pont de Nemours and Company), and 1,2-bis(1,1,2,2-tetrafluoroethoxy)ethane. High boiling solvents can be added, for example, xylene or other unsubstituted or substituted aromatic hydrocarbons; ethers such as benzyl ethyl ether, and dihexyl ether; glycol ethers such as diethyleneglycol monomethyl ether, and diethyleneglycol monoethyl ether; ketones such as acetonylacetone, and isophorone; alcohols such as 1-octanol, 1-nonanol, and benzylalcohol; esters such as benzyl acetate, ethyl benzoate, diethyl oxalate, diethyl maleate, ethylene carbonate, and propylene carbonate; and lactones such as γ-butyrolactone and δ-valerolactone. Alternatively, supercritical $CO_2$ may be useful as a solvent. These solvents may be used alone or in admixture of two or more. Typically, the solids content of the photoresist varies between 5 and 50 percent by weight of the total weight of the photoresist composition.

Other Components

The compositions of this invention can contain optional additional components. Examples of additional components which can be added include, but are not limited to, bases, surfactants, resolution enhancers, adhesion promoters, residue reducers, coating aids, plasticizers, and $T_g$ (glass transition temperature) modifiers.

Process Steps

For microlithography, the photoresist composition is applied to a suitable substrate such as a microelectronic wafer typically employed in the semiconductor industry. The solvent is then removed by evaporation.

Imagewise Exposure

The photoresist compositions of this invention are sensitive in the ultraviolet region of the electromagnetic spectrum and especially to those wavelengths ≦365 nm. Imagewise exposure of the photoresist compositions of this invention can be done at many different UV wavelengths including, but not limited to, 365 nm, 248 nm, 193 nm, 157 nm, and lower wavelengths. Imagewise exposure is preferably done with ultraviolet light of 248 nm, 193 nm, 157 nm, or lower wavelengths, more preferably with ultraviolet light of 193 nm, 157 nm, or lower wavelengths, and is still more preferably with ultraviolet light of 157 nm or lower wavelengths. Imagewise exposure can either be done digitally with a laser or equivalent device or non-digitally with use of a photomask. Digital imaging with a laser is preferred. Suitable laser devices for digital imaging of the compositions of this invention include, but are not limited to, argon-fluorine excimer lasers with UV output at 193 nm, krypton-fluorine excimer lasers with UV output at 248 nm, or fluorine (F2) lasers with output at 157 nm. Since, as discussed supra, use of UV light of lower wavelength for imagewise exposure corresponds to higher resolution (lower resolution limit), the use of a lower wavelength (e.g., 193 nm or 157 nm or lower) is generally preferred over use of a higher wavelength (e.g., 248 nm or higher). Specifically, imaging at 157 nm is preferred over imaging at 193 nm.

The photoresists of this invention are useful for 365 nm (1-line), 248 nm (KrF laser), and especially 193 nm (ArF laser) and 157 nm (F2laser) microlithography. For imaging at 193 and 157 nm, it is preferred that the polymer is substantially free of aromatic groups because these absorb significant amounts of light at these wavelengths. These photoresists are critical in allowing for the imaging of feature sizes in the submicron range.

Substrate

The substrate employed in this invention can be silicon, silicon oxide, silicon oxynitride, silicon nitride, or various other materials used in semiconductive manufacture. In a preferred embodiment, the substrate can be in the form of a microelectronic wafer. The microelectronic wafer can be prepared from silicon, silicon oxide, silicon oxynitride, or silicon nitride.

| GLOSSARY | |
|---|---|
| Analytical/Measurements | |
| bs | broad singlet |
| δ | NMR chemical shift measured in the indicated solvent |
| g | gram |
| h | hours |
| NMR | Nuclear Magnetic Resonance |
| $^1$H NMR | Proton NMR |
| $^{13}$C NMR | Carbon-13 NMR |
| $^{19}$F NMR | Fluorine-19 NMR |
| s | singlet |
| sec. | second(s) |
| m | multiplet |
| mL | milliliter(s) |
| mm | millimeter(s) |
| $T_g$ | Glass Transition Temperature |
| $M_n$ | Number-average molecular weight of a given polymer |
| $M_w$ | Weight-average molecular weight of a given polymer |
| $P = M_w/M_n$ | Polydispersity of a given polymer |
| Absorption coefficient | AC = A/b, where A, absorbance, = $Log_{10}(1/T)$ and b = film thickness in microns, where T = transmittance as defined below. |
| Transmittance | Transmittance, T, = ratio of the radiant power transmitted by a sample to the radiant power incident on the sample and is measured for a specified wavelength λ (e.g., nm). |
| Chemicals/Monomers | |
| CFC-113 | 1,1,2-Trichlorotrifluoroethane E. I. du Pont de Nemours and Company, Wilmington, DE |
| MAdA | 2-Methyl-2-adamantyl acrylate OHKA America, Inc., Milpitas, CA |
| NB-F-OH | ![structure] —OCH$_2$C(CF$_3$)$_2$OH |
| Perkadox ® 16 N | Di-(4-tert-butylcyclohexyl)peroxydicarbonate Noury Chemical Corp., Burt, NY |
| Solkane ® 365 mfc | 1,1,1,3,3-Pentafluorobutane Solvay Fluor, Hannover, Germany |
| t-BuAc | tert-Butyl acrylate Aldrich Chemical Company, Milwaukee, WI |
| TCB | Trichlorobenzene Aldrich Chemical Co., Milwaukee, WI |
| TCN-(O)(CF3)2 | ![structure] |

-continued

| GLOSSARY | |
|---|---|
| TCN-(O)(CF3, CO2CH3) | 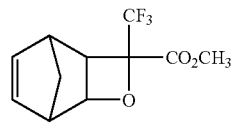 |
| TCN-(O)(CF3, CO2t-Bu) | 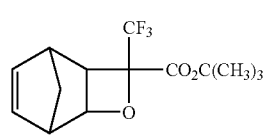 |
| TCN-(O), (C(CF3)2) | 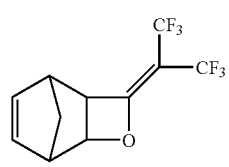 |
| TCN-(O)(c-C4F4Cl2) | 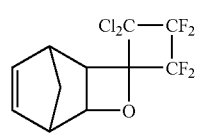 |
| TCN-(O)(CF3, CH2Br) | 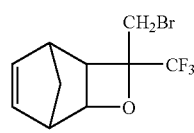 |
| TCN-(NH)(CF3)2 | 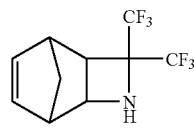 |
| TCN-(O)(CF3, Ph) | 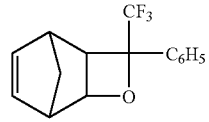 |
| TCN-(O)(F, CF2SO2F) | 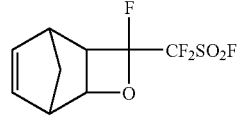 |
| TCN-(O)(OC(CF3)2) | 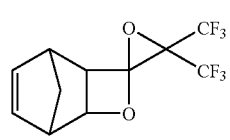 |
| TCN-(N)(CF3) | 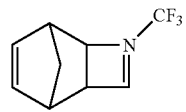 |
| TCN-(NC4F9)(F, C3F7) | 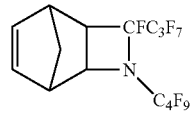 |

-continued

GLOSSARY

| | |
|---|---|
| TCN-(N(2-F—C6H4)) (CF3, CF3) | 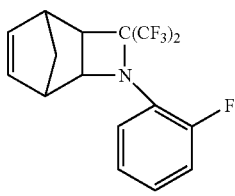 |
| TFE | Tetrafluoroethylene E. I. du Pont de Nemours and Company, Wilmington, DE |
| TCN-(O)(F2) | 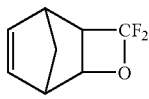 |
| THF | Tetrahydrofuran Aldrich Chemical Co., Milwaukee, WI |
| Ultraviolet | |
| Extreme UV | Region of the electromagnetic spectrum in the ultraviolet that ranges from 10 nanometers to 200 nanometers |
| Far UV | Region of the electromagnetic spectrum in the ultraviolet that ranges from 200 nanometers to 300 nanometers |
| UV | Ultraviolet region of the electromagnetic spectrum which ranges from 10 nanometers to 390 nanometers |
| Near UV | Region of the electromagnetic spectrum in the ultraviolet that ranges from 300 nanometers to 390 nanometers |

EXAMPLES

Unless otherwise specified, all temperatures are in degrees Celsius, all mass measurements are in grams, and all percentages are weight percentages, except for polymer compositions, which are expressed as mole % of the constitutent monomer repeat units.

Quadricyclane was prepared by photochemical isomerization of norbornadiene using procedure by C. D. Smith, published in *Organic Synthesis*, Collective Volume 6, p. 961. In all experiment quadricyclane of 85-95% purity (the remainder-norbornadiene) was used. $C_4F_9N=CFC_3F_7$ was prepared by catalytic cleavage of $(C_4F_9)_3N$ using reported synthesis by V. A. Petrov, G. G. Belen'kii, L. S. German Izv. *AN USSR*, 1985, p. 1934. $(CF_3)_2C=NH$ was prepared using reported synthesis by W. J. Midleton, C. G. Krespan *J. Org. Chem.* 1965, v. 30, p. 1398. $(CF_3)_2C=C=O$ was prepared using procedure by D. C. England and C. G. Krespan *J. Am. Chem. Soc.* 1965, v. 87, p. 4019; 2,2-dichloro3,3,4,4-terafluorocyclobutanone was prepared using procedure by D. C. England, U.S. Pat. No. 3,129,248 (to DuPont) (1964). $(CF_3)_2C=N$-(2-F—$C_6H_4$) was prepared according procedure by V. A. Petrov, D. D. Khasnis Israel *J. Chem.* 1999, v. 39, p. 147.

All other starting materials have been obtained from commercial sources and used without further purification.

Glass transition temperatures ($T_g$) were determined by DSC (differential scanning calorimetry) using a heating rate of 20° C./min, data is reported from the second heat. The DSC unit used is a Model DSC2910 made by TA Instruments, Wilmington, Del.

Assessment of 157 nm imaging sensitivity is done using a Lambda-Physik Compex 102 excimer laser configured for 157 nm operation. Vacuum ultraviolet transmission measurements are made using a McPherson spectrometer equipped with a D2 light source. Samples are spin-coated at several thicknesses on $CaF_2$ substrates, and the contribution of the substrate to the transmission is approximately removed by spectral division.

More specifically, all absorption coefficient measurements for polymers can be made using the procedure listed below.

1. Samples are first spin-coated on silicon wafers on a Brewer Cee (Rolla, Mo.), Spincoater/Hotplate model 100CB.

a) Two to four silicon wafers are spun at different speeds (e.g., 2000, 3000, 4000, 6000 rpm) to obtain differing film thickness and the coated wafers, are subsequently baked at 120° C. for 30 min. The dried films are then measured for thickness on a Gaertner Scientific (Chicago, Ill.), L116A Ellipsometer (400 to 1200 angstrom range). Two spin speeds are then selected from this data to spin the $CaF_2$ substrates for the spectrometer measurement.

b) Two $CaF_2$ substrates (1" dia.×0.80" thick) are selected and each is run as a reference data file on a McPherson Spectrometer (Chemsford, Mass.), 234/302 monochromer, using a 632 Deuterium Source, 658 photomultiplier, and Keithley 485 picoammeter.

c) Two speeds are selected from the silicon wafer data a) to spin the sample material onto the $CaF_2$ reference substrates (e.g., 2000 and 4000 rpm) to achieve the desired film thickness. Then each is baked at 120° C. for 30 min. and the sample spectra is collected on the McPherson Spectrometer; the sample files are then divided by the reference $CaF_2$ files.

d) The resulting absorbance files are then adjusted (sample film on $CaF_2$ divided by $CaF_2$ blank) for film thickness to give absorbance per micron (abs/mic), using GRAMS386 and KALEIDAGRAPH software.

The term "clearing dose" indicates the minimum exposure energy density (e.g., in units of mJ/cm$^2$) to enable a given photoresist film, following exposure, to undergo development.

Example 1

Preparation of TCN-(O)(CF3)2.

A 1 L flask equipped with a dry-ice condenser, thermometer and inlet tube was charged with 200 mL of dry ether, 115 g of quadricyclane (1 mol calculated for 80% purity quadricyclane, sample contained 15% ether and 5% norbornadiene). Gaseous hexafluoroacetone, 170 g (1.02 mol) was introduced in the flask at a rate that maintained the internal temperature below 33° C. (about 2 h). The reaction mixture was agitated at ambient temperature for 12 h, solvent was removed under vacuum and the residue (260 g) was distilled under vacuum to give 234 g (90.1%) of TCN-(O)(CF3)2; b.p. 66-67° C./26 mm Hg. $^{19}$F NMR (CDCl$_3$): −69.12 (3F, q; 10.3 Hz), −78.63(3F, q; 10.3 Hz) ppm; $^1$H NMR:1.60 (1H, d), 2.42 (1H, d), 2.60 (1H, d), 3.21 (2H, d), 4.75 (1H, d), 5.91 (1H, dd; 5.7, 3.0 Hz), 6.31 (1H, dd, 5.7; 3.4 Hz) ppm. Found: C, 46.25; H, 3.04; F, 44.31%.

Example 2

Preparation of TCN-(O)(CF3, CO2CH3)

TCN-(O)(CF3, CO2Me) was prepared using procedure for preparation of TCN-(O)(CF3)2 with the following exceptions: To 25 g of 80% quadricyclane (0.22 mol) in 60 mL of dry ether, 26 g (0.17 mol) of $CF_3C(O)C(O)OCH_3$ were added dropwise. TCN-(O)(CF3, CO2Me), 30 g (73%) was isolated; b.p. 119-121° C./19 mm Hg, as mixture of 2 isomers in ratio 1:2.3. $^{19}F$ NMR (CDCl$_3$): −80.00 (s, major isomer), −69.20 (s, minor isomer); IR:1754 (C═O) cm$^{-1}$. Found: C, 53.02; H, 4.61; F, 22.97%.

Example 3

Preparation of TCN-(O),(C(CF3)2)

TCN-(O),(C(CF3)2) was prepared by adding 53 (0.3 mol) g of gaseous $(CF_3)_2C$═C═O to a solution of 32 g (0.28 mol) of 80% quadricyclane in 200 mL of dry ether at 30-35° C. After removal of solvent, and vacuum distillation of crude product (75 g), 55 g (73%) of TCN-(O),(C(CF3)2) were isolated; b.p. 98-99° C./19 mm. $^{19}F$ NMR (CDCl$_3$): −58.07 (3F, m), −53.15 (3F, m) ppm; $^1H$ NMR:1.75(1H, d), 1.85 (1H, d), 3.13(1H, s), 3.29(1H, s), 3.50 (1H, m), 4.96(1H, d), 5.01(1H, dd; 5.7, 3.5 Hz), 6.34(1H, dd, 5.4; 2.7 Hz) ppm; IR: 1687 (C═C) cm$^{-1}$ Found: C, 48.60; H. 2.89; F, 42.63%.

Example 4

Preparation of TCN-(O)(c-C4F4Cl2)

TCN-(O)(c-C4F4Cl2) was prepared by slow addition (~1 h) of 2,2-dichloro3,3,4,4-tetrafluorocyclobutanone (20 g, 0.094 mol) to 11 g of quadricyclane at 30-35° C. The reaction mixture was agitated overnight and the crude product (30 g) was distilled under vacuum to give 23 g (77%) of TCN-(O)(c-C4F4Cl2) as a mixture of two isomers (ratio 77:33), b.p. 83.5-84.5° C./0.06 mm. $^{19}F$ NMR (CDCl$_3$), major: −116.9 (1F, ddd; 201, 10, 2 Hz), −120.4 (1F, dd; 201, 6 Hz), −120.2 (2F, AB pattern, $J_d$=230 Hz); minor:: −116.8 (1F, ddd; 115 Hz), −119.1 (1F, dd; 115 Hz), −121.55 (1F, ddd; 220; 9; 1 Hz); −126.6(1F, ddd; 220; 13; 9 Hz) ppm.

Example 5

Preparation of TCN-(O)(CF3, CH2Br)

This compound was prepared in the same manner as TCN-(O)(CF3, CO2Me), using 60 g of $CF_3C(O)CH_2Br$ and 40 g of quadricyclane at 25-90° C. (3 h). Isolated was 74 g (87%) of TCN-(O)(CF3, CH2Br); b.p. 65-66° C./0.07 mm as a mixture of two isomers in the ratio 1:1.4. $^{19}F$ NMR (CDCl$_3$): major: −80.37 (s) ppm, minor: −69.88 (s) ppm. Found: C, 41.85; H, 3.40; F, 19.99%.

Example 6

Preparation of TCN-(NH)(CF3)2

A mixture of 50 g (0.3 mol) of $(CF_3)_2C$═NH, 40 g of quadricyclane (80% purity, 0.35 mol) in 100 mL of dry ether was kept at 100° C. for 12 h. Fractionation of the crude product afforded 3 g of TCN-(NH)[(CF3)2], as a mixture with TCN(O)(CF3)2 (ratio 36:64), b.p. 47-49° C./40 mm Hg (two isomers, ratio 92:8). $^{19}F$ NMR (CDCl$_3$): major −70.3 (3F, q; 11.5 Hz), −77.5 (3F, q; 11.5 Hz) ppm; minor (−72.0 (3F, dq), −77.5 (3F) ppm. $^1H$ NMR(CDCl$_3$): 1.5(1H, d), 2.3(2H, m), 2.6 (1H), 2.8 (1H, s), 3.0 (1H, s), 3.8 (1H, t), 5.9 (1H, dd), 6.2(1H, dd) ppm. IR (KCl, neat): 3357 (NH) cm$^{-1}$. GC/MS: 258 (M+, $C_{10}H_9F_6N^+$).

Example 7

Preparation of TCN-(O)(CF3, Ph)

This compound was prepared by refluxing (90-110° C., 18 h) a mixture of 17.4 g (0.1 mol) of $CF_3C(O)C_6H_5$ and 12 mL of quadricyclane, followed by vacuum distillation. Isolated was 15.1 g (57%) of TCN-(O)(CF3, Ph), b.p. 82-83° C./0.13 mm Hg, as a mixture of two isomers in a ratio of 3:1. $^{19}F$ NMR (CDCl$_3$), major: −82.16 (s); minor −72.45 (s) ppm; Found. C, 67.69; H, 4.83; F, 21.31%.

Example 8

Preparation of TCN-(O)(F, CF2SO2F)

$FC(O)CF_2SO_2F$ (72 g, 0.4 mol) was slowly added (~2 h) to 50 mL of quadricyclane at 20-30° C. The reaction mixture was agitated at ambient temperature for 2 h and distilled under vacuum to give 100 g (92%) of TCN-(O)(F, CF2SO2F), b.p. 75-76° C./0.7 mm Hg, as a mixture of two isomers in the ratio 66:34. $^{19}F$ NMR (CDCl$_3$), major: 45.14 (1F, m), −111.11(1F, dt; 247; 3.9 Hz), −113.46(1F, dt; 246 Hz), −119.27(1F, m); minor: 42.94(1F, m), −96.85(1F, t; 12.3 Hz), −104.58(1F, dt; 246.3; 5.8), −107.56(1F, dt; 246.3; 4.5 Hz) ppm. IR (KCl, neat): 1442 cm$^{-1-}$. Found. C, 39.54; H, 2.96%.

Example 9

Synthesis of a TFE, TCN-(O)(CF3)2 Polymer

A 200 mL stainless steel pressure vessel was charged with 63.2 g TCN-(O)(CF3)2, 50 mL of Solkane® 365 mfc and 2.2 g of Perkadox® 16N initiator. The vessel was closed, cooled in dry ice, purged with nitrogen, evacuated, and charged with 45.5 g of TFE. The vessel was then agitated with its contents at 50° C. for 18 hr while the internal pressure decreased from 340 to 250 psi. The vessel was cooled to room temperature and vented to 1 atmosphere. The vessel contents were removed using additional Solkane® 365 mfc to rinse. The gelled mass was dissolved by the addition of 70 mL of THF. This solution was added to excess hexane (30-35 mL portion to 650 mL hexane). The precipitated polymer was washed with hexane, air-dried for several hours and then dried overnight in a vacuum oven with slight nitrogen purge at 88-90° C. There was 1 isolated 52.0 g of white polymer; GPC analysis: Mn 5900, M$_w$ 14600. T$_g$ 210° C. (DSC). Anal. Found: C, 41.21%; H, 2.22%; F, 51.13%; $^{19}F$ NMR (δ, THF-d8) −64 (3F from TCN-(O)(CF3)2), −78 (3F from TCN-(O)(CF3)2), −95 to −125 (4F from TFE).

Example 10

Synthesis of a TFE, TCN-(O)(C(CF3)2) Polymer

A 200 mL stainless steel pressure vessel was charged with 54.0 g TCN-(O)(C(CF3)2), 50 mL of Solkane® 365 mfc and 1.6 g of Perkadox® 16N initiator. The vessel was closed, cooled in dry ice, purged with nitrogen, evacuated, and charged with 30 g of TFE. The vessel was then agitated with its contents at 50° C. for 18 hr while the internal pressure decreased from 269 to 190 psi. The vessel was cooled to room temperature and vented to 1 atmosphere. The vessel contents were removed using additional Solkane® 365 mfc to rinse. This solution was added to excess hexane (30-35 mL portion to 650 mL hexane). The precipitated polymer was washed with hexane, air dried for several hours and then dried overnight in a vacuum oven with slight nitrogen purge at 88-90° C. There was isolated 44.8 g of white polymer; GPC analysis: Mn 12400, $M_w$ 22400. $T_g$ 236° C. (DSC). Anal. Found: C, 43.06%; H, 2.10%; F, 48.91%. $^{19}$F NMR (δ, THF-d8) −57.5 (6F from TCN-(O)(C(CF3)2)), −95 to −125 (4F from TFE).

Example 11

Synthesis of a TFE, TCN-(O)(CF3, CO2CH3) Polymer

A 200 mL stainless steel pressure vessel was charged with 23.0 g TCN-(O)(CF3, CO$_2$CH3), 50 mL of Solkane® 365 mfc and 0.8 g of Perkadox® 16N initiator. The vessel was closed, cooled in dry ice, purged with nitrogen, evacuated, and charged with 15 g of TFE. The vessel was then agitated with its contents at 50° C. for 18 hr. The vessel was cooled to room temperature and vented to 1 atmosphere. The vessel contents were removed using additional Solkane® 365 mfc to rinse. This solution was added to excess hexane (30-35 mL portion to 650 mL hexane). The precipitated polymer was washed with hexane, air dried for several hours and then dried overnight in a vacuum oven with slight nitrogen purge at 88-90° C. There was isolated 12.6 g of white polymer; GPC analysis: Mn 5000, $M_w$ 9100. $T_g$ 109° C. (DSC). Anal. Found: C, 50.00%; H, 3.92%; F, 32.05%. $^{19}$F NMR (δ, THF-d8)-(3F from TCN-(O)(CF3, CO2CH3)), −95 to −125 (4F from TFE).

Example 12

Synthesis of a TFE. TCN-(O)(F, CF2SO2F) Polymer A 200 mL stainless steel pressure vessel was charged with 54.4 g TCN-(O)(F, CF2SO2F), 50 mL of Solkane® 365 mfc and 1.59 g of Perkadox® 16N initiator. The vessel was closed, cooled in dry ice, purged with nitrogen, evacuated, and charged with 30 g of TFE. The vessel was then agitated with its contents at 50° C. for 18 hr. The vessel was cooled to room temperature and vented to 1 atmosphere. The vessel contents were removed using additional Solkane® 365 mfc to rinse. This solution was added to excess hexane (30-35 mL portion to 650 mL hexane). The precipitated polymer was washed with hexane, air-dried for several hours and then dried overnight in a vacuum oven with slight nitrogen purge at 88-90° C. There was isolated 41.0 g of white polymer; GPC analysis: Mn 5600, $M_w$ 13500. $^{19}$F NMR (δ, THF-d8)+40 to 45 (SO2F), −85 to −125 (remaining fluorines from both monomers). Anal. Found: C, 37.32%; H, 2.39%; F, 36.41%.

Example 13

Synthesis of TCN-(O)(OC(CF3)2)

To an agitated solution of sodium hypochlorite in water (prepared by addition of 25 g chlorine gas to the mixture of 50 mL of 50 wt. % of sodium hydroxide and 200 mL of water at −5 to 0° C.) was added 0.5 g of (C$_4$H$_9$)$_4$NHSO$_4$ followed by slow addition (~15 min) of the solution of 50 g (0.185 mol) of TCN-(O)(OC(CF3)2) (prepared as in Example 3) in 100 mL of ether at 0° C. The reaction mixture was warmed to ambient temperature over 1 h and agitated for 14 h. The upper layer was separated, the water layer was extracted with ether (100 mL×1), the combined organic fractions were dried over MgSO$_4$ and solvent was removed under vacuum at 20-25° C. to leave 58 g of crude product, containing ~20% of ether. The residue was kept under dynamic vacuum at ambient temperature for 40 min. There was isolated 52 g (calculated yield 98%) of slightly yellow TCN-(O)(OC(CF3)2) oxide containing ~2% ether. This material was used for polymerization without further purification. A sample of TCN-(O)(OC(CF3)2) oxide (23.5 g, 80% purity, the remainder, ether) prepared in a separate experiment was distilled under vacuum to give 18 g (65% isolated yield) of pure TCN-(O)(OC(CF3)2) oxide, b.p. 32-34° C./0.1 mm. $^{19}$F NMR (CDCl$_3$): −68.1 (3F, q; 8 Hz), −70.1(3F, q; 8 Hz) ppm. $^1$H NMR (CDCl$_3$): 1.8(1H, d; 10 Hz), 2.0(1H, d; 10 Hz), 3.0(1H, s), 3.1(1H, d), 3.3(1H, s), 4.7(1H, dd; 5; 2 Hz), 6.0(1Hdd), 6.3(1H, dd) ppm. IR (KCl, liquid film): 1681 (w), 1452 (s) cm$^{-1}$. Anal.: Found: C, 45.61; H, 2.77; F, 39.88%. $C_{11}H_8F_6O_2$.

Example 14

Synthesis of a TFE. TCN-(O)(OC(CF3)2) Polymer

A 200 mL stainless steel pressure vessel was charged with 16.1 g TCN-(O)(OC(CF3)2), 50 mL of Solkane® 365 mfc and 0.57 g of Perkadox® 16N initiator. The vessel was closed, cooled in dry ice, purged with nitrogen, evacuated, and charged with 12 g of TFE. The vessel was then agitated with its contents at 50° C. for 18 hr. The vessel was cooled to room temperature and vented to 1 atmosphere. The vessel contents were removed using additional Solkane® 365 mfc to rinse. This solution was added to excess hexane (30-35 mL portion to 650 mL hexane). The precipitated polymer was washed with hexane, air-dried for several hours and then dried overnight in a vacuum oven with slight nitrogen purge at 88-90° C. There was isolated 12.5 g of white polymer; GPC analysis: $M_n$ 7700, $M_w$ 13800. $^{19}$F NMR (δ, THF-d8) −68.0 and −70.2 (CF$_3$ from TCN-(O)(OC(CF3)2), −95 to −125 ppm (CF$_2$ from TFE). Anal. Found: C, 37.32; H, 2.39; F, 36.41%.

Example 15

Preparation of TCN-(N)(CF3)

A mixture of 24 g g (0.25 mol) of CF$_3$CN, 35 g of quadricyclane (95% purity) was loaded in Hastelloy reactor and kept at 100° C. for 12 h. Fractionation of the crude product using short spinning band column afforded 38 g (78%) of TCN-(N)(CF3), b.p. 54-55.2° C./13 mm Hg. $^{19}$F NMR (CDCl$_3$): −73.8 (3F, d; 2 Hz) ppm; $^1$H NMR (CDCl$_3$): 1.3 (1H, d; 10 Hz), 1.6(1H, d; 10 Hz), 2.7(1H, s), 3.0(2H, d), 3.8(1H, s), 6.2 (2H, m) ppm; $^{13}$C NMR(neat): 36.7, 39.8, 40.1, 47.2, 66.4, 118.4(q, 276 Hz), 134.5, 137.0, 180(q, 38 Hz) ppm; IR (KCl, neat): 2978(s), 1615(w), 1564(w), 1460 (w) cm$^{-1}$. MS: 187(M$^+$, C$_9$H$_8$F$_3$N$^+$), 186(C$_9$H$_7$F$_3$N$^+$).

Example 16

Preparation of TCN-(O)(F2)

A mixture of 20 g g (0.3 mol) of F$_2$C=O, 35 g of quadricyclane (95% purity) and 100 mL of dry ether was loaded in Hastelloy reactor and kept at 40° C. for 10 h. The solvent was removed under vacuum and the residue (47 g) was distilled under vacuum afforded 11 g (23%) of TCN-(O)(F2), b.p. ° C./13 mm Hg, [96% purity, contaminated with 4% of 3 unidentified compounds (ratio 55:39:4), isomeric to TCN-(O)(F2) (GC/MS)]. $^{19}$F NMR (CDCl$_3$): −61.6

(1F, dd; 112; 5 Hz); −70.8 (1F, ddd; 112; 13; 4 Hz) ppm; $^1$H NMR (CDCl$_3$): 1.6(1H, d; 10 Hz), 2.1(1H, d; 10 Hz), 2.9(1H, m), 2.9(1H, d), 3.0(1H, s), 3.2(1H, s), 4.3(1H, ddm; 13; 5; 2 Hz), 6.0 (1H, dd; 6; 3 Hz), 6.3 (1H, dd; 6; 3 Hz) ppm; $^{13}$C NMR(neat): 38.5(d; 5 Hz), 40.6(dd; 4; 2 Hz), 44.2(d; 4 Hz), 48.4(dd; 26; 29 Hz), 122.9 (dd, 284; 289 Hz), 132.6(s), 139.0(s) ppm. IR (KCl, neat):1464(m) cm$^{-1}$. GC/MS: 158(M$^+$, C$_8$H$_8$F$_2$O$^+$).

Example 17

Preparation of TCN-(NC4F9)(F, C3F7)

A mixture of 8.6 g (0.02 mol) of C$_4$F$_9$N═CFC$_3$F$_7$ and 3 g of quadricyclane (95% purity) was kept in glass reactor at 25° C. for 2 d. The fractionation of crude reaction mixture under vacuum afforded 6.4 g (61%) of TCN-(NC4F9)(F, C3F7) b.p. 53-54° C./0.05 mm Hg, as a mixture of two isomers (ratio 88:12). Found: C, 34.12; H, 1.51; F, 61.09, N, 2.69%. IR (KCl, neat): 1467 (w) cm$^{-1}$.

Example 18

Preparation of TCN-(N(2-F—C6H4))(CF3, CF3)

A mixture of 2.6 g (0.01 mol) of (CF$_3$)$_2$C═N-(2-F—C$_6$H$_4$) and 3 g of quadricyclane (85% purity) was kept in glass reactor at 90° C. for 50 h. The fractionation of crude reaction mixture under vacuum afforded 0.5 g (14%) of TCN-(N(2-FC6H4)) (CF3, CF3) b.p. 76-78° C./0.1 mm Hg, as a mixture of two isomers (ratio 98:2). $^{19}$F NMR (CDCl$_3$), major: −64.2 (3F, m; 9 Hz), −72.9(3F, dq; 9; 4 Hz), −128.6 (1F, m) ppm; minor: −64.2 (3F), −79.9(3F), −133.9(1F, m) ppm; $^1$H NMR (CDCl$_3$), major: 1.5(1H, d), 2.4(2H, m), 3.2(2H, d), 4.3(1H, m), 6.1 (1H, dd); 6.3(1H, dd), 6.9(2H, m), 7.0(2H, m) ppm; minor: 1.6(1H, d), 2.4(2H, m), 3.2(2H, d), 4.8(1H, m), 6.1 (1H, dd); 6.3(1H, dd), 6.9 (2H, m), 7.0 (2H, m) ppm; IR (KCl, neat): 1506; 1456 cm$^{-1}$; C$_{16}$H$_{12}$F$_7$N. Found: C, 54.41; H, 3.34; F, 37.30, N, 4.18%.

The description of illustrative and preferred embodiments of the present invention is not intended to limit the scope of this invention. Various modifications, alternative constructions and equivalents may be employed without departing from the true spirit and scope of the appended claims.

What is claimed is:

1. An ethylenically unsaturated compound having the structure:

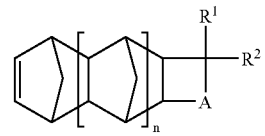

(I)

wherein n is 0, 1, or 2;
A is O or NR$^3$;
R$^1$ and R$^2$ are independently H; halogen; C$_1$-C$_{10}$ alkyl or alkoxy, optionally substituted by halogen or ether oxygen; C$_6$-C$_{20}$ aryl; Y; C(R$_f$)(R$_f'$)OR$^4$; R$^5$Y; OR$^5$Y; and
R$^3$ is H; C$_1$-C$_{10}$ alkyl or alkoxy, optionally substituted by halogen o'r ether oxygens; C$_6$-C$_{26}$ aryl; Y; C(R$_f$)(R$_f'$)OR$^4$; R$^5$Y; OR$^5$Y; or
R$^1$ and R$^2$ taken together are ═C(R$_f$)(R$_f'$) or C$_2$-C$_9$ alkylene, optionally substituted by halogen or incorporating an ether oxygen; or
R$^2$ and R$^3$ taken together are part of a double bond;
Y is COZ or SO$_2$Z;
R$^4$ is hydrogen or an acid-labile protecting group;
R$_f$ and R$_f'$ are the same or different fluoroalkyl groups of 1 to 10 carbon atoms or taken together are (CF$_2$)$_m$ where m is 2 to 10;
R$^5$ is a C$_1$-C$_{20}$ alkylene group, optionally substituted by halogen or ether oxygen;
Z is OH, halogen, R$^6$ or OR$^6$; and
R$^6$ is a C$_1$-C$_{20}$ alkyl group, optionally substituted by halogen or ether oxygens; or C$_6$-C$_{20}$ aryl;
with the proviso that at least one of R$^1$ or R$^2$ is fluorine or contains one or more fluorine atoms.

2. The ethylenically unsaturated compound of claim 1, wherein n is 0 and A is oxygen.

3. The ethylenically unsaturated compound of claim 2, wherein R$^1$ and R$^2$ are perfluoroalkyl groups of 1 to 10 carbon atoms or taken together are (CF$_2$)$_m$ where m is 2 to 10.

4. The ethylenically unsaturated compound of claim 2, wherein R$^1$ is CF$_3$ and R$^2$ is COOR$^6$.

* * * * *

UNITED STATES PATENT AND TRADEMARK OFFICE
CERTIFICATE OF CORRECTION

PATENT NO. : 7,326,796 B2  Page 1 of 1
APPLICATION NO. : 10/523489
DATED : February 5, 2008
INVENTOR(S) : Andrew Edward Feiring et al.

It is certified that error appears in the above-identified patent and that said Letters Patent is hereby corrected as shown below:

Title page,
After item (22), insert:
-- Related U.S. Application Data
(60) Provisional Application No. 60/402261, filed on August 9, 2002. --

Signed and Sealed this

Eighth Day of July, 2008

JON W. DUDAS
*Director of the United States Patent and Trademark Office*